(12) United States Patent
Stirton

(10) Patent No.: US 6,618,149 B1
(45) Date of Patent: Sep. 9, 2003

(54) METHOD OF IDENTIFYING FILM STACKS BASED UPON OPTICAL PROPERTIES

(75) Inventor: James Broc Stirton, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 0 days.

(21) Appl. No.: 09/827,534

(22) Filed: Apr. 6, 2001

(51) Int. Cl.[7] ............................................... G01N 21/55
(52) U.S. Cl. ................................................... 356/445
(58) Field of Search ........................... 356/445–447, 356/600–613

(56) References Cited

U.S. PATENT DOCUMENTS

| | | | |
|---|---|---|---|
| 4,625,114 A | * 11/1986 | Bosacchi et al. | ......... 250/341.4 |
| 5,457,727 A | * 10/1995 | Frijlink | ................. 378/73 |
| 5,867,276 A | 2/1999 | McNeil et al. | ............... 356/445 |
| 5,877,860 A | 3/1999 | Borden | ..................... 356/376 |
| 5,880,838 A | 3/1999 | Marx et al. | ................... 356/351 |
| 6,051,348 A | 4/2000 | Marinaro et al. | ............. 430/30 |
| 6,081,334 A | 6/2000 | Grimbergen et al. | ....... 356/357 |
| 6,245,584 B1 | 6/2001 | Marinaro et al. | ............. 438/14 |

* cited by examiner

Primary Examiner—Tu T. Nguyen
(74) Attorney, Agent, or Firm—Williams, Morgan & Amerson, P.C.

(57) ABSTRACT

A method of determining the composition of a film stack using optical properties is disclosed herein. In one embodiment, the method comprises providing a library of optical characteristic traces, each of which correspond to a film stack combination comprised of multiple process layers, providing a wafer having a film stack formed thereabove, and illuminating the film stack. The method further comprises measuring light reflected off the film stack to generate an optical characteristic trace for the film stack, and determining the composition of the film stack formed above the wafer by correlating or matching the generated optical characteristic trace for the film stack above the wafer to an optical characteristic trace from the library, the optical characteristic trace from the library having an associated film stack composition comprised of a plurality of known process layers.

15 Claims, 3 Drawing Sheets

METHOD OF IDENTIFYING FILM STACKS BASED UPON OPTICAL PROPERTIES

BACKGROUND OF THE INVENTION

1. Field of the Invention

This invention relates generally to semiconductor fabrication technology, and, more particularly, to a method of identifying film stacks based upon optical properties, and a system for accomplishing same.

2. Description of the Related Art

By way of background, modern integrated circuit devices, e.g., microprocessors, ASICs, memory devices, etc., are comprised of millions of field effect transistors formed on a semiconducting substrate, such as silicon. The substrate may be doped with either N-type or P-type dopant materials. An illustrative field effect transistor 10, as shown in FIG. 1, may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown).

The gate electrode 14 has a critical dimension 12, i.e., the width of the gate electrode 14, that approximately corresponds to the channel length 13 of the device when the transistor 10 is operational. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

In general, semiconductor manufacturing operations involve, among other things, the formation of layers of various materials, e.g., polysilicon, insulating materials, etc., and the selective removal of portions of those layers by performing known photolithographic and etching techniques. These processes are continued until such time as the integrated circuit device is complete. Additionally, although not depicted in FIG. 1, a typical integrated circuit device is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The precise combination of steps used in manufacturing integrated circuit devices, e.g, so-called process flows, may change over time as technological advances and/or equipment improvements occur. In some cases, multiple layers of material are formed to define a film stack from which various features of a transistor may be formed. For example, in forming gate electrodes for transistor devices, one process flow might involve the formation of a layer of silicon dioxide (which will ultimately become the gate insulation layer 16) that is grown in a dry furnace process, a doped layer of polysilicon (which will ultimately become the gate electrode 14), and an anti-reflecting coating (ARC) layer comprised of silicon nitride. These layers will ultimately be subjected to one or more processing operations, e.g., etching, to define various components of the transistor, e.g., the layer of polysilicon may be patterned to define the gate electrode 14. Subsequent improvements in materials, manufacturing techniques and/or design may lead to changes in the process flows used to make such transistors. For example, in another process flow, the polysilicon layer from which the gate electrodes will be formed may be changed such that it is comprised of an undoped polysilicon, and the ARC layer may be changed to silicon oxynitride. Moreover, the thickness of the various layers of the film stack may vary from one process flow to another.

Unfortunately, several process flows may be in use in a given fabrication facility at any one time. That is, film stacks on which processing operations are to be performed, e.g., etching, may be comprised of different layers of materials having differing thicknesses. Such a situation occurs because, in most fabrication facilities, a new process flow is not implemented throughout the entire facility in a wholesale fashion. Given that preexisting process flows produce devices of acceptable quality, production managers are, understandably, reluctant to make wholesale changes in the manufacturing operation, despite the fact that a new process flow may have been extensively tested prior to its introduction into a manufacturing environment. Typically, such new process flows tend to gradually be introduced and used until such time as later developed, improved process flows are introduced.

As a result, there may be several different film stacks being produced in the fabrication facility at any given time. Unfortunately, these variations may lead to problems in the manufacturing of integrated circuits. For example, in an extreme case, an etching process may be performed on what is assumed to be a film stack comprised of a layer of polysilicon and a layer of silicon nitride, when, in fact, the film stack is comprised of a layer of polysilicon and a layer of silicon oxynitride. If such an event were to occur, then the etching process may render the resulting product unusable or at least cause extensive rework to be performed. Such problems result in expensive delays, cost overruns, and a general decrease in the yield of semiconductor manufacturing operations.

The present invention is directed to a method and system that may solve, or at least reduce, some or all of the aforementioned problems.

SUMMARY OF THE INVENTION

The present invention is generally directed to a method of identifying film stacks based upon optical properties, and a system for accomplishing same. In one illustrative embodiment, the method comprises determining the composition of a film stack by providing a library of optical characteristic traces, each of which correspond to a film stack combination, providing a wafer having a film stack formed thereabove, and illuminating the film stack. The method further comprises measuring light reflected off the film stack to generate an optical characteristic trace for the film stack, and determining the composition of the film stack formed above the wafer by correlating or matching the generated optical characteristic trace for the film stack above the wafer to an optical characteristic trace from the library, the optical characteristic trace from the library having an associated film stack composition comprised of a plurality of known process layers.

In another illustrative embodiment, the method comprises determining the composition of a film stack by providing a library of optical characteristic traces, each of which correspond to a film stack combination comprised of a known combination of process layers formed above a known grating structure, providing a wafer having a film stack formed above said known grating structure, and illuminating the film stack and the known grating structure. The method further comprises measuring light reflected off the film stack and the known grating structure to generate an optical characteristic trace for the film stack and the known grating structure, and determining the composition of the film stack formed above the wafer by correlating or matching the generated optical characteristic trace for the film stack and the known grating structure to an optical characteristic trace from the library, the optical characteristic trace from the library having an associated film stack combination comprised of a plurality of known process layers formed above said known grating structure.

BRIEF DESCRIPTION OF THE DRAWINGS

The invention may be understood by reference to the following description taken in conjunction with the accompanying drawings, in which like reference numerals identify like elements, and in which.

Figure 1:
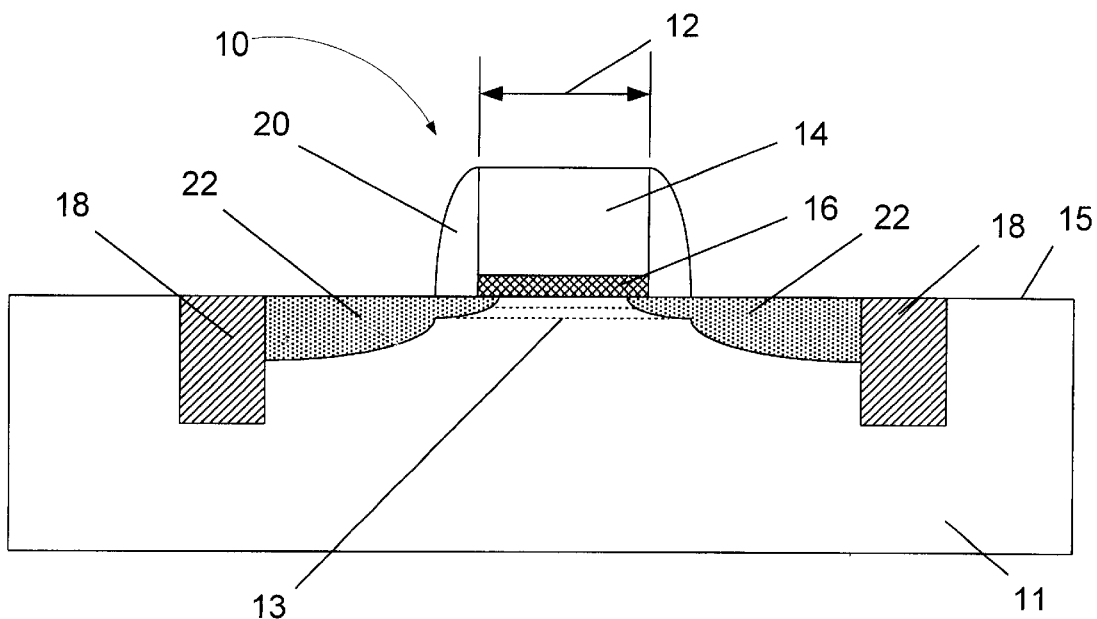
FIG. 1 is a cross-sectional view of an illustrative prior art transistor.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention.

In general, the present invention is directed to a method of identifying the composition of film stacks based upon optical properties, and a system for accomplishing same. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc.

Semiconductor manufacturing generally involves multiple processes whereby one or more layers of material are formed above a semiconducting substrate, and portions of those layers are selectively removed until such time as a completed device is formed. In general, photolithography involves the process of forming a layer of photoresist material above one or more process layers in which a feature, e.g., a metal line, a gate electrode, an opening in a layer of insulating material, will be formed. Thereafter, a pattern that is desired to be transferred into the underlying process layer or layers will be formed in the layer of photoresist material. Then, using one or more etching processes, the underlying process layers are etched using the patterned layer of photoresist as a mask, thereby resulting in a patterned process layer that replicates the pattern formed in the layer of photoresist.

Such process layers may be comprised of any type of material commonly encountered in semiconducting processing, e.g., polysilicon, metal, e.g., aluminum, an insulating material, e.g., silicon dioxide, HSQ, a layer of material having a dielectric constant greater than 3, a positive or negative type photoresist material, etc. Moreover, the process layers may be formed by a variety of techniques used to form such materials, e.g., chemical vapor deposition (CVD), physical vapor deposition (PVD), thermal growth, spin-coating, etc., and the thickness of the process layers may vary greatly.

After a complete reading of the present application, those skilled in the art will understand that the present invention may be employed in a vast variety of situations involving a vast number of possible combinations of process layers. Nevertheless, for purposes of explanation, the present invention will be discussed in the context of two particular process flows whereby gate electrode structures are patterned from a layer of polysilicon.

Figure 2:
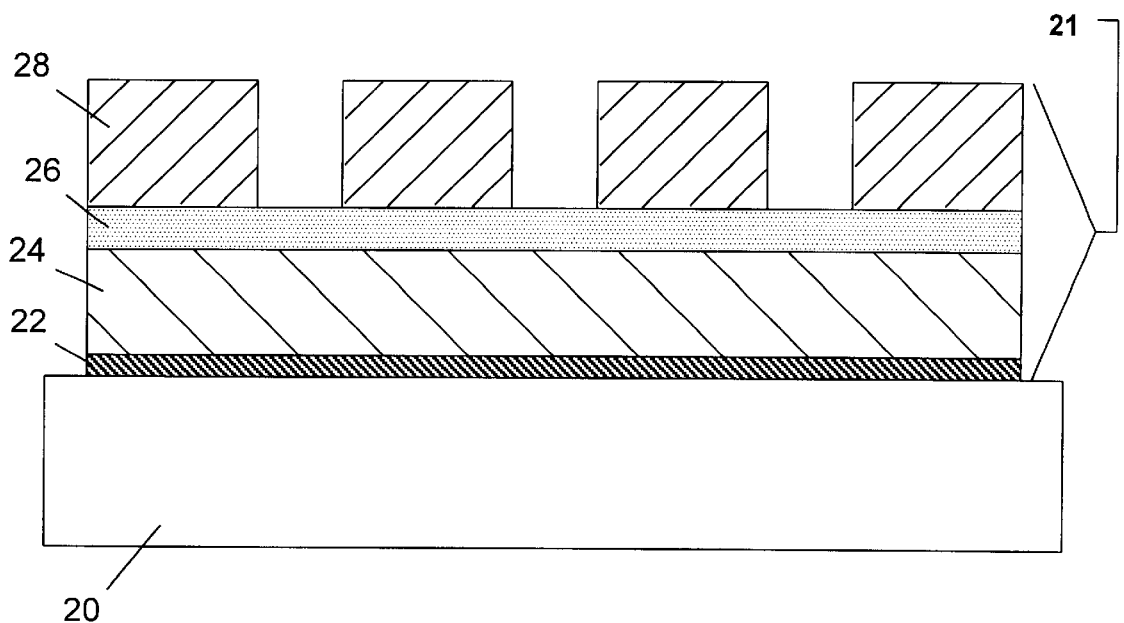
FIG. 2 is a cross-sectional view of an illustrative film stack combination.

As shown in FIG. 2, illustrative process layers 22, 24, 26 and 28 are formed above a structure 20. The process layers 22, 24, 26 and 28 are intended to depict an illustrative film stack 21 that will be subjected to additional processing operations in a semiconductor manufacturing facility. In the depicted embodiment, the process layer 22 is comprised of silicon dioxide, the process layer 24 is comprised of polysilicon, the process layer 26 is comprised of an anti-reflective coating ("ARC") material, and the process layer 28 is a patterned layer of photoresist. As will be readily apparent to those skilled in the art after reading the present application, the structure 20 may be a semiconducting substrate, e.g., a silicon wafer, or it may represent one or more previously formed layers of material above such a semiconducting substrate, e.g., a stack of insulating layers each having a plurality of conductive interconnections formed therein.

The various process layers depicted in FIG. 2 may be formed by a variety of techniques, and may be made from a variety of materials. For example, the layer of silicon dioxide comprising the process layer 22 may be formed by a thermal growth process in a wet or dry furnace, and it may have a thickness ranging from approximately 2–5 nm (20–50 Å). The polysilicon material comprising the process layer 24 may be either undoped or doped with an appropriate dopant material, e.g., arsenic, boron, and it may be formed by a deposition process to a thickness ranging from approximately 150–300 nm (1500–3000 Å). The process layer 26 may be comprised of a variety of anti-reflective coating materials, e.g., silicon nitride (SiN), silicon oxynitride (SiON), and it may be formed by a deposition process to a thickness ranging from approximately 30–50 nm (300–500 Å). The process layer 28 may be comprised of either a positive or negative type photoresist, and it may have a thickness ranging from approximately 400–1000 nm (4,000–10,000 Å).

The above described variations in the various process layers 22, 24, 26, 28 may result in a variety of possible or probable film stacks 21 combinations. Each of these film stack 21 combinations may exhibit a unique optical characteristic trace due to the variation in the values of reflectivity, index of refraction ("n") and dielectric constant ("k") of the various process layers comprising the film stack 21. Such variations may be due to thickness variations, material variation and/or methods of manufacture. In general, the present invention is directed to forming a library containing optical characteristic traces for a plurality of probable film stack 21 combinations that may be encountered in the semiconductor manufacturing facility. In turn, this library of optical characteristic traces is used to determine, distinguish and/or confirm the composition of the film stack 21 that is to be subjected to subsequent processing operations, for example, an etching process, or other types of semiconductor manufacturing processes. In one particular implementation of the present invention, the library will contain optical characteristic traces for all film stack 21 combinations that are likely to be encountered in a particular semiconductor manufacturing facility.

Based upon the above description of the process layers 22, 24, 26, 28, there are several possible film stack 21 combinations that may be subjected to processing operations in the fabrication facility. The layers that comprise the film stack 21 may vary in material, thickness, method of manufacture, etc., all of which tend to vary the optical characteristics of film stack 21. Table I is a chart depicting one illustrative example of possible combinations for the film stack 21 for the process flows discussed above. As shown therein, for a particular process layer, a thickness range is established that corresponds to the expected thickness values for the process layer and a resolution, or incremental value, for the thickness range is established. For example, the process layer 24 comprised of doped polysilicon has an anticipated thickness range of approximately 150–300 nm (1500–3000 Å) and a resolution of approximately 30 nm. Thus, the process layer 22 has six probable thickness values (150, 180, 210, 270, 300 nm). Similar calculations may be made for the other possible layers in the embodiment described herein. The resolution selected for each layer may be varied as a matter if design choice. Obviously, the finer the resolution, the larger the number of film combinations, and the larger the library comprised of optical characteristic traces for each such combination. As indicated in Table I, based upon the possible materials, the anticipated thickness ranges and the selected resolution values, there are 36,288 possible process layer combination for the film stack 21 based upon the process flows described above.

TABLE I

| Layer Number | Description | Anticipated Thickness Range (nm) | Resolution (nm) | Number of Possible Variations |
|---|---|---|---|---|
| 22 | SiO$_2$ (dry) | 2–5 | 1 | 4 |
| 22 | SiO$_2$ (wet) | 2–5 | 1 | 4 |
| 24 | Poly (doped) | 150–300 | 30 | 6 |
| 24 | Poly (undoped) | 150–300 | 30 | 6 |
| 26 | SiON | 30–50 | 10 | 3 |
| 26 | SiN | 30–50 | 10 | 3 |
| 28 | Photoresist | 400–1000 | 100 | 7 |
| | Total Combinations | | | 36,288 |

Through use of the present invention, a signature or optical characteristic trace may be established for a vast variety, if not all, probable combinations of film stacks 21 readily anticipated by the design process. In the illustrative example set forth in Table I, an optical characteristic trace may be generated for each of the 36,288 probable combinations of the film stack 21. The optical characteristic trace for a given film stack 21 may be based on a variety of characteristics or factors, including, but not limited to, the thickness, the index of refraction ("n"), the dielectric constant ("k"), and/or the reflectivity of one or more of the individual process layers that make up the film stack 21. The optical characteristic trace may be generated using a variety of optical metrology tools to be discussed more fully below.

Variations in one or more of the optical characteristics of the process layers in the film stack 21, e.g., index of refraction, will cause a significant change in the diffraction characteristics of the incident light from a light source of an optical metrology tool. Thus, a unique optical characteristic trace may be established for each unique combination of film stacks 21 anticipated by the design process. A library of optical characteristic traces corresponding to each unique combination of anticipated film stacks 21 may be calculated (using Maxwell's equations). Obviously, the number of combinations used to create the library may vary as a matter of design choice. Moreover, the greater the number of combinations, the greater will be the library containing the appropriate signature profiles of the film stack characteristics.

Figure 3:
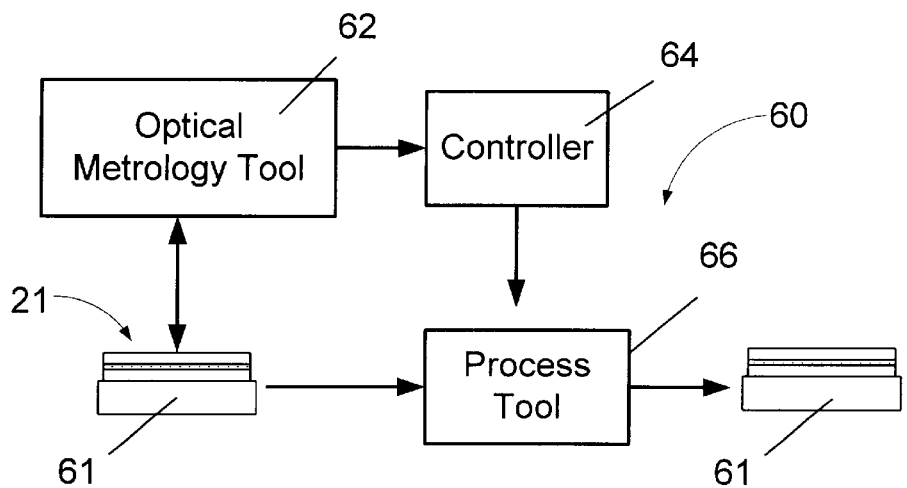
FIG. 3 depicts an illustrative embodiment of a system in accordance with one embodiment of the present invention.

An illustrative system 60 that may be used in one embodiment of the present invention is shown in FIG. 3. The system 60 is comprised of an optical metrology tool 62, a process tool 66, and a controller 64. The process tool 66 is meant to be illustrative in nature in that it may represent any type of processing tool commonly found in modem semiconductor manufacturing facilities, e.g., an etching tool, a stepper tool, etc.

As indicated in FIG. 3, one or more wafers 61, having an illustrative film stack 21 comprised of multiple process layers, which may or may not include a layer of photoresist formed thereabove, are provided to the optical metrology tool 62. Thereafter, using the optical metrology tool 62, one or more of the optical characteristics, e.g., reflectivity, the index of refraction ("n"), and/or the dielectric constant ("k"), of the film stack 21 that is to be processed in the process tool 66 is determined. That is, the optical metrology tool 62 may be used to generate an optical characteristic trace for the film stack 21 on the wafers 61 to be processed in the process tool 66. The optical metrology tool 62 may be any type of tool useful for measuring or determining the desired optical characteristics of the film stack 21. For example, the optical metrology tool 62 may be a spectroscopic ellipsometer, a reflectometer or a scatterometer.

The number of and location of the optical measurements taken of the incoming film stack 21 may be varied as a matter of design choice. For example, such measurements may be performed on all wafers in one or more lots, or on a representative number of wafers in a given lot, and these results may then be used to determine the composition of the incoming film stack 21. The more measurements taken, the higher degree of likelihood that the measurements actually reflect the true optical characteristics of the incoming film stack 21. The responsible process engineer may decide on an appropriate number of measurements to be taken, as well as the location of those measurements consistent with the degree of confidence desired by the process engineer with respect to the particular application under consideration.

Through use of the present invention, a library comprised of optical characteristic traces is established for a variety, if not all, probable film stack 21 combinations. This library of traces may be stored in a database that is readily accessible by the controller 64 and/or the optical metrology tool 62. Based upon the unique optical characteristic trace of each unique film stack combination, the present invention may be used to confirm or determine the composition of an incoming film stack 21. For example, the optical metrology tool 62 will generate an optical characteristic trace of a film stack 21 comprised of unknown process layers. This generated optical characteristic trace will then be compared or correlated to optical characteristic traces in the library containing probable known combinations of film stacks 21 to determine the best fit or match. Based upon this comparison or correlation, the incoming film stack 21 is determined to have a combination of process layers that corresponds to or closely approximates the known process layer combinations of the matched optical characteristic trace from the library. Thus, knowing the composition of the incoming film stack 21, the controller 64 can confirm/select the appropriate processing recipe for the film stack 21 in the process tool 66. For example, if the incoming film stack 21 is determined to be comprised of a combination of the following combination of layers, $SiO_2$/Poly/SiN/Photo, the controller 64 can determine that the process recipe, e.g., an etch recipe, to be performed in the process tool 66 is appropriate for the determined film stack 21 combination. Alternatively, if the controller 64 determines that a preselected process recipe to be performed in the process tool 66 is incorrect for the identified composition of the film stack 21, it may change the recipe to be performed in the process tool 66, or it may generate an alarm to advise operators within the manufacturing facility of the apparent discrepancy.

Figure 4A:
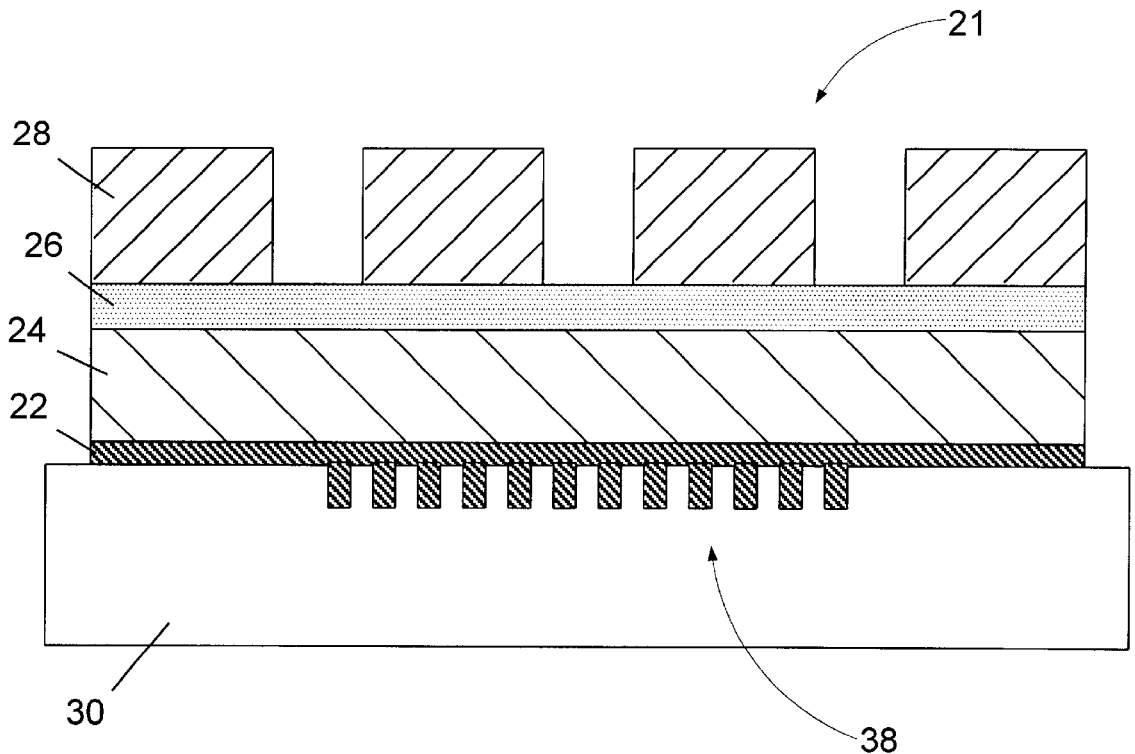
FIGS. 4A–4C depict an illustrative embodiment of the present invention in which an illustrative grating structure may be used.
Figure 4B:
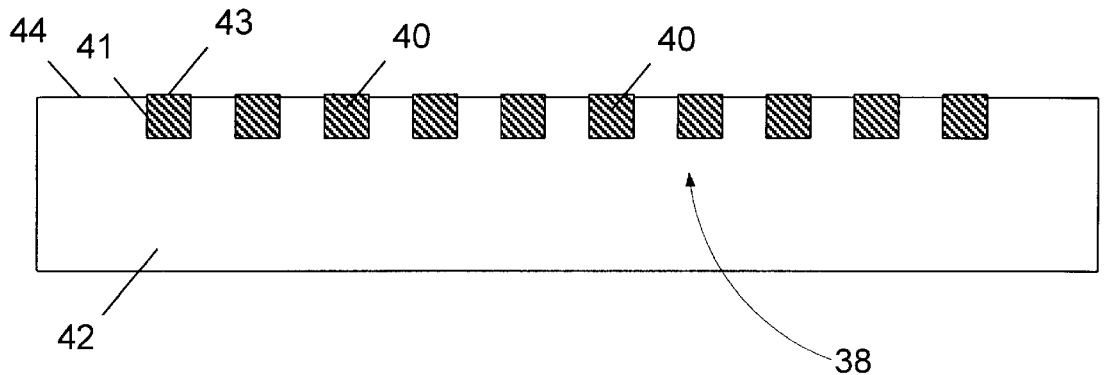
Figure 4C:
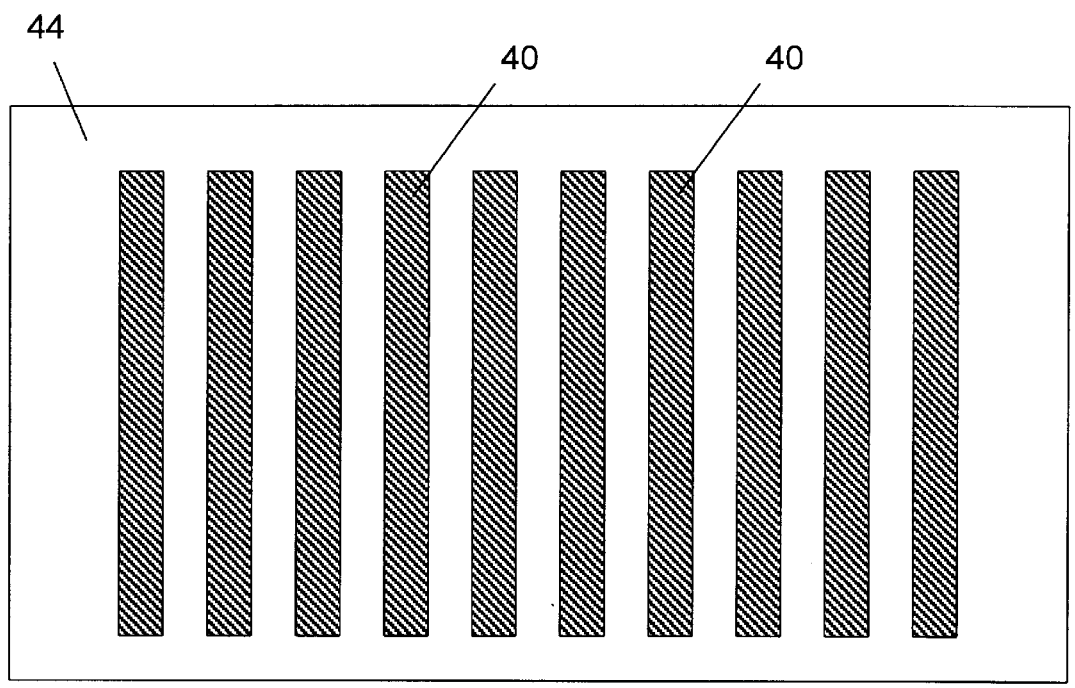

In another illustrative embodiment, a grating structure 38 may be used in the present invention. As shown in FIGS. 4A–C, a grating structure 38 may be formed in the structure 30 prior to forming the film stack 21, such as the illustrative process layers 22, 24, 26, 28, depicted in FIG. 4A. The grating structure 38 may be formed in a scribe line of semiconducting substrate, and it may take a variety of forms. In one illustrative embodiment, as shown in FIGS. 4B–C, the grating structure 38 is comprised of a plurality of trench isolation regions 40 formed in a semiconducting substrate 42. The trench isolation structure 40 may be formed by a variety of known techniques, e.g., by etching a plurality of trenches 41 in the substrate 42, and filling the trenches 41 with an appropriate insulating material, such as silicon dioxide. The isolation regions 40 may have an upper surface 43 that extends above a surface 44 of the substrate 42. The number of isolation regions 40 that may be formed on an actual device may vary. For example, the grating structure 38 may be formed in a 100 nm×120 nm region in which approximately 300–400 isolation regions 40 are formed (the length of which are parallel to the short side of the region).

As stated previously, scatterometric techniques may also be used to measure the optical characteristics of the film stack 21. A variety of scatterometry type tools may be used with the present invention, e.g., so-called 2θ-type systems and lens-type scatterometry tools. The scatterometry tool 24 may use white light, or some other wavelength or combination of wavelengths, depending on the specific implementation. Typically, the scatterometry tool will generate an incident beam that has a wide spectral composition and wherein the intensity of the light changes slowly in comparison to changes in wavelength. The angle of incidence of the light may also vary, depending on the specific implementation. For example, a spectroscopic ellipsometer (single angle, many wavelengths), or a laser (single wavelength, many angles) may be used with the present invention. Additionally, the light source and the detector may be arranged in a concentric circle configuration, with the light source illuminating the structure from a perpendicular orientation, e.g., a reflectometer. The intensity of the reflected light may be measured as s- and p-polarization over either multiple angles or at multiple wavelengths.

In general, the scatterometry tool 24 includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc.

In this embodiment of the present invention, a library of optical characteristic traces may be calculated (using Maxwell's equations) for all probable combinations of the film stack 21 that may be formed above the grating structure 38. In this embodiment, an unknown film stack 21 combination is formed over the grating structure 38. Thereafter, the optical metrology tool 62 generates an optical characteristic trace of the grating structure 38 having the unknown film stack 21 formed thereabove. Scatterometry libraries are commercially available from Timbre Technologies, Inc. The generated optical characteristic trace of the grating structure 38 and unknown film stack is then compared to the library containing optical characteristic traces for the grating structure 38 with various known film stack 21 combinations formed thereabove. Based upon an identification of which optical characteristic trace best matches the generated or measured trace of the grating structure 38 and the unknown film stack, the composition of the incoming film stack 21 may be determined.

In the illustrated embodiments, the controller 64 is a computer programmed with software to implement the functions described herein. Moreover, the functions described for the controller 64 may be performed by one or more controllers spread through the system. For example, the controller 64 may be a fab level controller that is used to control processing operations throughout all or a portion of a semiconductor manufacturing facility. Alternatively, the controller 64 may be a lower level computer that controls only portions or cells of the manufacturing facility. Moreover, the controller 64 may be a stand-alone device, or it may reside on the process tool 66 or on a photolithography module (not shown). However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 64, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699 Provisional Specification for CIM Framework Domain Architecture) and APC (SEMI E93-0999—Provisional Specification for CIM Framework Advanced Process Control Component) specifications are publicly available from SEMI.

The present invention is generally directed to a method of identifying film stacks based upon optical properties. In one illustrative embodiment, the method comprises providing a library of optical characteristic traces, each of which correspond to a film stack combination comprised of a plurality of process layers, providing a wafer having a film stack formed thereabove, and illuminating the film stack. The method further comprises measuring light reflected off the film stack to generate an optical characteristic trace for the film stack, and determining the composition of the film stack formed above the wafer by correlating or matching the generated optical characteristic trace for the film stack above the wafer to an optical characteristic trace from the library, the optical characteristic trace from the library having an associated film stack composition comprised of a known combination of process layers.

In another illustrative embodiment, the method comprises determining the composition of a film stack by providing a library of optical characteristic traces, each of which correspond to a film stack combination comprised of a known combination of process layers formed above a known grating structure, providing a wafer having a film stack formed above said known grating structure, and illuminating the film stack and the known grating structure. The method further comprises measuring light reflected off the film stack and the known grating structure to generate an optical characteristic trace for the film stack and the known grating structure, and determining the composition of the film stack formed above the wafer by correlating or matching the generated optical characteristic trace for the film stack and the known grating structure to an optical characteristic trace from the library, the optical characteristic trace from the library having an associated film stack combination comprised of a plurality of known process layers formed above said known grating structure.

The present invention is also directed to a system that may be used in performing the methods described above. In one illustrative embodiment, the method comprises an optical metrology tool 62 that generates an optical characteristic trace for a film stack comprised of an unknown combination of process layers, and a controller that compares and matches the generated optical characteristic trace to one or more optical characteristic traces in a library, each of which correspond to a known film stack combination, and thereby determines the composition of the unknown film stack combination. In another illustrative embodiment, the system is adapted to determine the composition of an unknown combination of process layers formed above a known grating structure.

Through use of the present invention, better process control may be achieved in modem integrated circuit manufacturing facilities. More particularly, the present invention allows the determination/confirmation of the composition of a variety of possible film stack combinations that may be in use in a semiconductor manufacturing facility. Moreover, this identification may be made possible by the creation of a universal library wherein optical characteristics of all probable film stack combinations may be maintained. This library may be readily accessible by a number of controllers used in modern semiconductor fabrication facilities, thereby enhancing control operations throughout the manufacturing plant. All of which benefits lead to an overall increase in production efficiency and product yields.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of determining the composition of a film stack, comprising:
   providing a library of optical characteristic traces, each of which correspond to a film stack combination comprised of a known combination of process layers formed above a known grating structure;
   providing a wafer having a film stack formed above said known grating structure;
   illuminating said film stack and said known grating structure;

measuring light reflected off the film stack and said known grating structure to generate an optical characteristic trace for said film stack and said known grating structure; and determining the composition of the film stack formed above said known grating structure by correlating the generated optical characteristic trace for said film stack and said known grating structure to an optical characteristic trace from said library, the optical characteristic trace from said library having an associated film stack composition comprised of a known combination of process layers formed above said known grating structure.

2. The method of claim 1, wherein providing a library of optical characteristic traces, each of which correspond to a film stack combination comprised of a known combination of process layers above a known grating structure comprises providing a library of optical characteristic traces, each of which correspond to a film stack combination, each film stack combination being comprised of at least one of a layer of metal, a layer of polysilicon, a layer of silicon dioxide, a layer of silicon nitride, a layer of silicon oxynitride and a layer of photoresist material.

3. The method of claim 1, wherein providing a wafer having a film stack formed above said known grating structure comprises providing a wafer having a film stack formed above said known grating structure, each film stack being comprised of at least one of a layer of metal, a layer of polysilicon, a layer of silicon dioxide, a layer of silicon nitride, a layer of silicon oxynitride and a layer of photoresist material.

4. The method of claim 1, further comprising determining if the determined composition of said film stack above said known grating structure is appropriate for a subsequent processing operation to be performed on said film stack above said known grating structure at a processing tool.

5. The method of claim 1, further comprising initiating an alarm if said determined composition of said film stack above said known grating structure is inappropriate for a subsequent processing operation to be performed on said film above said known grating structure stack at a processing tool.

6. The method of claim 1, wherein illuminating said film stack comprises illuminating said film stack using at least one of a spectroscopic ellipsometer, a reflectometer, and a scatterometer.

7. The method of claim 1, wherein providing a library of optical characteristic traces comprises providing a library of optical characteristic traces based upon at least one of a reflectivity, an index of refraction and a dielectric constant of at least some of said known process layers comprising said film stack combination.

8. The method of claim 1, wherein providing a library of optical characteristic traces comprises:

calculating an optical characteristic trace for each probable film stack combination; and storing each of said traces in a library.

9. A method of determining the composition of a film stack, comprising:

providing a library of optical characteristic traces, each of which correspond to a film stack combination comprised of a known combination of a plurality of process layers formed above a known grating structure;

providing a wafer having a film stack formed above said known grating structure, said film stack being comprised of at least one of a layer of metal, a layer of polysilicon, a layer of silicon dioxide, a layer of silicon nitride, a layer of silicon oxynitride and a layer of photoresist material;

illuminating said film stack and said known grating structure;

measuring light reflected off the film stack and the known grating structure to generate an optical characteristic trace for said film stack and said known grating structure; and determining the composition of the film stack formed above said known grating structure by correlating the generated optical characteristic trace for said film stack and said known grating structure to an optical characteristic trace from said library, the optical characteristic trace from said library having an associated film stack composition comprised of a known combination of process layers formed above said known grating structure.

10. The method of claim 9, wherein providing a library of optical characteristic traces, each of which correspond to a film stack combination comprised of a known combination of process layers formed above a known grating structure comprises providing a library of optical characteristic traces, each of which correspond to a film stack combination, each film stack combination being comprised of at least one of a layer of metal, a layer of polysilicon, a layer of silicon dioxide, a layer of silicon nitride, a layer of silicon oxynitride and a layer of photoresist material.

11. The method of claim 9, further comprising determining if the determined composition of said film stack above said known grating structure is appropriate for a subsequent processing operation to be performed on said film stack above said known grating structure at a processing tool.

12. The method of claim 9, further comprising initiating an alarm if said determined composition of said film stack above said known grating structure is inappropriate for subsequent processing operations at a processing tool.

13. The method of claim 9, wherein illuminating said film stack comprises illuminating said film stack using at least one of a spectroscopic ellipsometer, a reflectometer, and a scatterometer.

14. The method of claim 9, wherein providing a library of optical characteristic traces comprises providing a library of optical characteristic traces based upon at least one of a reflectivity, an index of refraction and a dielectric constant of at least some of said plurality of process layers comprising said film stack combination above said known grating structure.

15. The method of claim 9, wherein providing a library of optical characteristic traces comprises:

calculating an optical characteristic trace for each probable film stack combination above said known grating structure; and storing each of said traces in a library.

* * * * *

UNITED STATES PATENT AND TRADEMARK OFFICE
CERTIFICATE OF CORRECTION

PATENT NO. : 6,618,149 B1 Page 1 of 1
DATED : September 9, 2003
INVENTOR(S) : James Broc Stirton It is certified that error appears in the above-identified patent and that said Letters Patent is hereby corrected as shown below:

<u>Title page,</u>
Item [*] Notice, "by 0 days" should read -- by 160 days --

Signed and Sealed this

Sixth Day of January, 2004

JAMES E. ROGAN
*Director of the United States Patent and Trademark Office*